(12) United States Patent
Overmyer

(10) Patent No.: US 10,251,716 B2
(45) Date of Patent: Apr. 9, 2019

(54) ROBOTIC SURGICAL SYSTEM WITH SELECTIVE MOTION CONTROL DECOUPLING

(71) Applicant: Ethicon LLC, Guaynabo, PR (US)

(72) Inventor: Mark D. Overmyer, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 332 days.

(21) Appl. No.: 15/383,017

(22) Filed: Dec. 19, 2016

(65) Prior Publication Data

US 2018/0168754 A1    Jun. 21, 2018

(51) Int. Cl.
G05B 19/04    (2006.01)
G05B 19/18    (2006.01)
(Continued)

(52) U.S. Cl.
CPC ........ *A61B 34/35* (2016.02); *A61B 17/00234* (2013.01); *A61B 34/25* (2016.02); *A61B 34/37* (2016.02); *A61B 34/74* (2016.02); *A61B 46/10* (2016.02); *A61B 90/37* (2016.02); *B25J 9/1689* (2013.01); *A61B 17/068* (2013.01);
(Continued)

(58) Field of Classification Search
CPC ............ A61B 17/00234; A61B 17/068; A61B 2017/00115; A61B 2017/00199; A61B 2017/00212; A61B 2034/302; A61B 2034/741; A61B 2034/742; A61B 34/25;
(Continued)

(56) References Cited

U.S. PATENT DOCUMENTS 6,459,926 B1 * 10/2002 Nowlin ................. A61B 34/70
600/102
6,799,065 B1 * 9/2004 Niemeyer .......... A61B 1/00149
600/407
(Continued)

FOREIGN PATENT DOCUMENTS

WO    WO-2013018933 A1    2/2013
WO    WO-2014151621 A1    9/2014
(Continued)

OTHER PUBLICATIONS

U.S. Appl. No. 15/200,283 entitled "Methods, Systems, And Devices For Initializing A Surgical Tool" filed on Jul. 1, 2016.
(Continued)

*Primary Examiner* — Harry Y Oh
(74) *Attorney, Agent, or Firm* — Mintz Levin/EES

(57) ABSTRACT

Robotic surgical systems are provided for control of an end effector in response to actuation of a user interface device based upon different control states. In each control state, selected movement directions of the user interface device are either coupled to or decoupled from corresponding movements directions of the end effector. Decoupled movement directions can be recoupled by positioning the user interface device within a range of where the user interface device and the end effector were decoupled. To assist with such recoupling, a graphical image estimating a position of the end effector that would be achieved, based upon a current position of the user interface device, if the decoupled movement direction was recoupled can be overlaid upon a current position of the end effector.

22 Claims, 10 Drawing Sheets

(51) Int. Cl.
*A61B 34/35* (2016.01)
*B25J 9/16* (2006.01)
*A61B 34/00* (2016.01)
*A61B 17/00* (2006.01)
*A61B 46/10* (2016.01)
*A61B 90/00* (2016.01)
*A61B 34/37* (2016.01)
*A61B 34/30* (2016.01)
*A61B 17/068* (2006.01)

(52) U.S. Cl.
CPC ..... *A61B 34/76* (2016.02); *A61B 2017/00115* (2013.01); *A61B 2017/00199* (2013.01); *A61B 2017/00212* (2013.01); *A61B 2034/302* (2016.02); *A61B 2034/741* (2016.02); *A61B 2034/742* (2016.02); *A61B 2034/743* (2016.02); *A61B 2034/744* (2016.02)

(58) Field of Classification Search
CPC ......... A61B 34/35; A61B 34/37; A61B 34/74; A61B 34/76
See application file for complete search history.

(56) References Cited

U.S. PATENT DOCUMENTS

| | | | |
|---|---|---|---|
| 8,114,345 | B2 | 2/2012 | Dlugos, Jr. et al. |
| 9,345,552 | B2 * | 5/2016 | Janik ................ A61B 17/32002 |
| 9,492,927 | B2 * | 11/2016 | Diolaiti ................. B25J 9/1689 |
| 9,622,826 | B2 * | 4/2017 | Diolaiti .................... B25J 9/161 |
| 9,636,185 | B2 * | 5/2017 | Quaid ..................... G06F 19/00 |
| 9,717,563 | B2 * | 8/2017 | Tognaccini ........ A61B 1/00183 |
| 2009/0036902 | A1 * | 2/2009 | DiMaio .................. A61B 34/10 |
| | | | 606/130 |
| 2009/0088774 | A1 | 4/2009 | Swarup et al. |
| 2013/0245375 | A1 | 9/2013 | DiMaio et al. |
| 2014/0276952 | A1 * | 9/2014 | Hourtash ............... B25J 9/1638 |
| | | | 606/130 |
| 2014/0276953 | A1 * | 9/2014 | Swarup .................. B25J 18/007 |
| | | | 606/130 |
| 2015/0313676 | A1 * | 11/2015 | Deodhar .............. A61B 17/295 |
| | | | 606/130 |
| 2017/0136624 | A1 * | 5/2017 | Hourtash ............... B25J 9/1607 |
| 2017/0172672 | A1 * | 6/2017 | Bailey ................... A61B 34/30 |
| 2017/0273748 | A1 * | 9/2017 | Hourtash ............... A61B 34/30 |
| 2018/0168758 | A1 * | 6/2018 | Lutzow ................. A61B 34/30 |

FOREIGN PATENT DOCUMENTS

| | | |
|---|---|---|
| WO | WO-2014151952 A1 | 9/2014 |
| WO | WO-2015175278 A1 | 11/2015 |
| WO | WO-2016194539 A1 | 12/2016 |

OTHER PUBLICATIONS

U.S. Appl. No. 15/237,648 entitled "Methods, Systems, And Devices For Causing End Effector Motion With A Robotic Surgical System" filed on Aug. 16, 2016.
U.S. Appl. No. 15/237,653 entitled "Methods, Systems, And Devices For Controlling A Motor Of A Robotic Surgical System" filed on Aug. 16, 2016.
U.S. Appl. No. 15/282,243 entitled "User Input Device For Robotic Surgical System" filed on Sep. 30, 2016.
U.S. Appl. No. 15/282,353 entitled "System And Method Of Converting User Input Into Motion Of A Surgical Instrument Via A Robotic Surgical System" filed on Sep. 30, 2016.
International Search Report and Written Opinion for International App. No. PCT/IS2017/064425 dated Apr. 4, 2018 (14 pages).

* cited by examiner

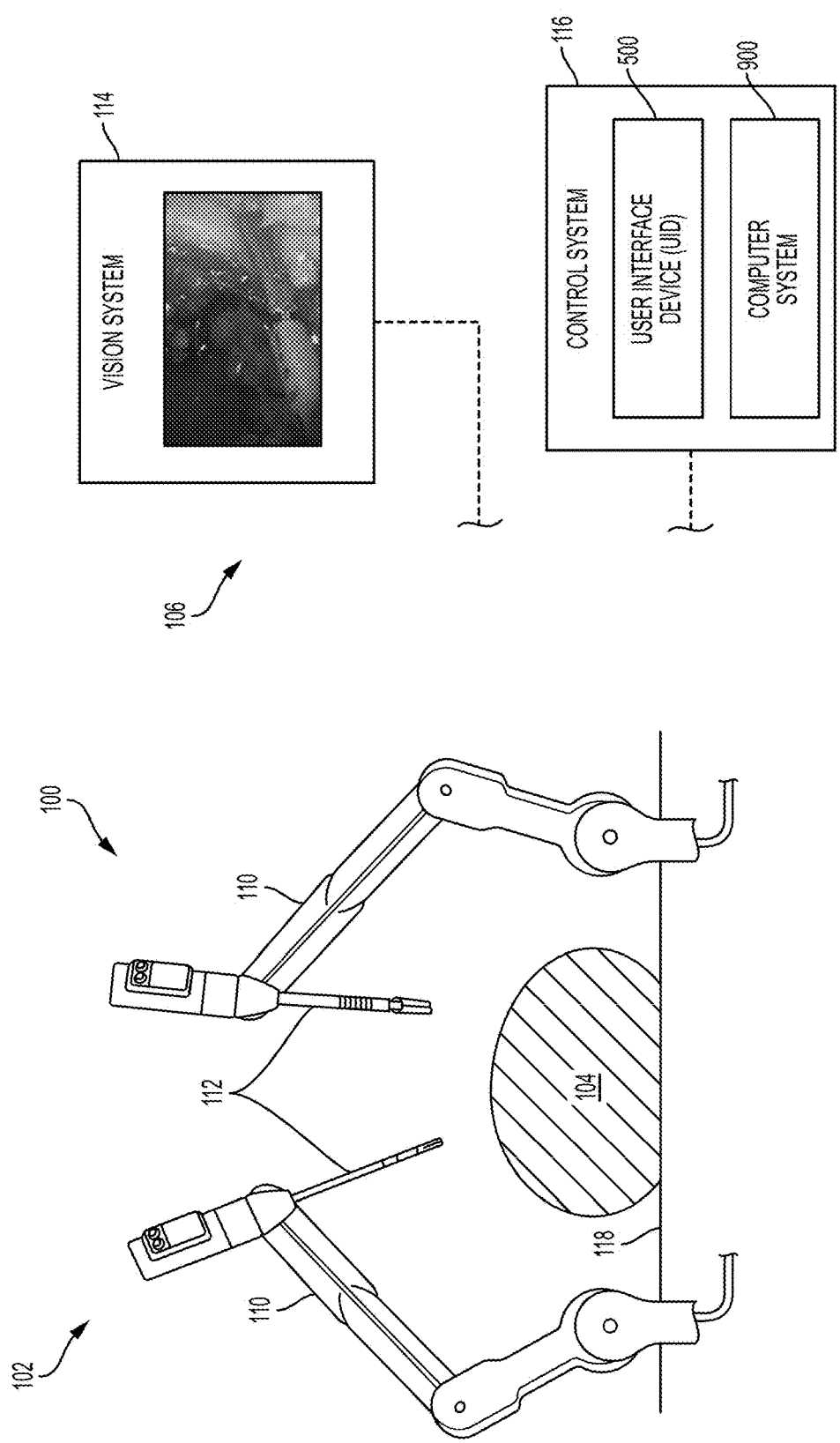

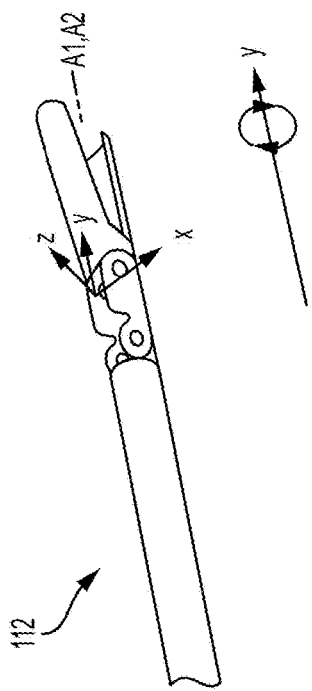
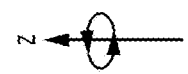
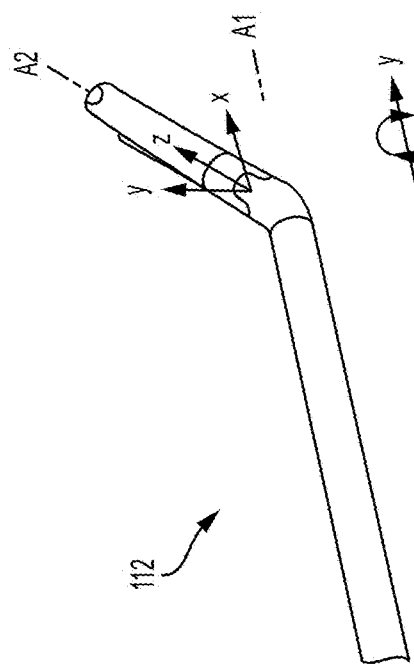
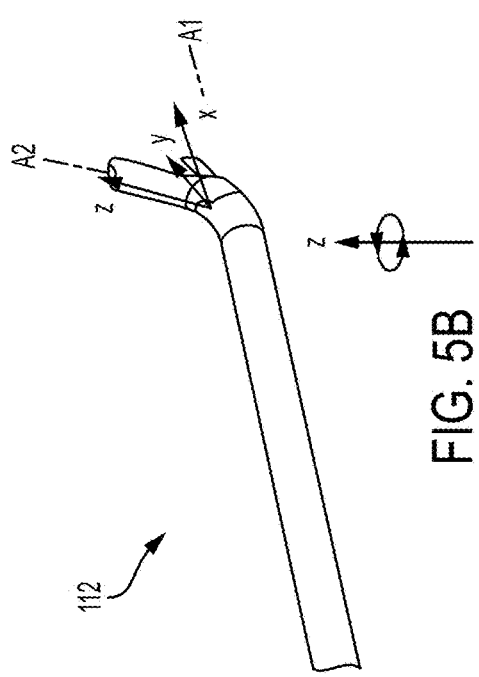
FIG. 5B
FIG. 5C
FIG. 5D

ROBOTIC SURGICAL SYSTEM WITH SELECTIVE MOTION CONTROL DECOUPLING

FIELD

Methods and devices are provided for robotic surgery and, in particular, techniques for motion control of robotic surgical tools using hand-held devices.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a tele-surgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Thus, while significant advances have been made in the field of robotic surgery, there remains a need for improved methods, systems, and devices for use in robotic surgery.

SUMMARY

In an embodiment, a surgical system is provided. The surgical system includes an electromechanical tool, an electromechanical arm, and a control system. The electromechanical tool includes an instrument shaft and an end effector formed on the instrument shaft and the end effector can be configured to perform a plurality of surgical functions on tissue of a patient. The electromechanical arm is configured for movement with respect to multiple axes and the electromechanical tool is configured to be mounted on, and move relative to, the electromechanical arm. The control system is further configured to control movement and surgical functions of the end effector according to at least two control states in response to actuation of a user interface device. In a first control state, a movement of the user interface device in a first selected direction effects a corresponding movement of the end effector in the first selected direction. In a second control state, a movement of the user interface device in the first selected direction does not effect a corresponding movement of the end effector in the first selected direction and the end effector performs a first surgical function in response to receipt of a first surgical function input by the user interface device. The control system is additionally configured to move to the second control state from the first control state in response to receipt of a first transition input by the user interface device.

In some embodiments, one or more of the following features can be optionally included in the system. For example, the control system is configured to move to the first control state from the second control state when a second transition input is received by the user interface device and a current position of the user interface device with respect to the first selected direction during the second control state is within a tolerance of a prior position of the user interface device with respect to the first selected direction when the second control state was entered from the first control state. The system further includes a vision system configured to display a current end effector position and a graphical representation of an estimated end effector position according to the current position of the user interface device. In the first control state, movement of the end effector corresponds to movement of the user interface device in any direction. The control system is configured to control movements and surgical functions of the end effector according to a third control state in response to receipt of a third transition input by the user interface device, and, in the third control state, movement of the user interface device in a second selected direction, different from the first selected direction, does not result in a corresponding movement of the end effector in the second selected direction and the end effector performs a third surgical function, different from the second surgical function, in response to receipt of a third surgical function input by the user interface device. The control system is configured to prohibit entry of the third control state from the second control state prior to performance of the second surgical function. The control system enters the second control state from the third control state when a fourth transition input is received by the user interface device and a current position of the user interface device during the third control state is within a tolerance of a prior position of the user interface device with respect to the second selected direction when the third control state was entered from the second control state. The third surgical function can include at least two sequentially performed surgical functions and the control system is configured to prohibit transition from the third control state to the second control state until each of the at least two surgical functions of the third surgical function is performed. The first surgical function includes clamping the tissue and the second surgical function includes deploying a plurality of staples to the tissue. The control system is configured to prohibit entry of the first control state from the third control state. The second transition input, the third transition input and the fourth transition input can include modulation of the first transition input.

In another embodiment, a method of controlling a surgical robot is provided. The method includes receiving, by a computing device, an actuation signal corresponding to actuation of a user interface device. The method also includes generating, by the computing device, a plurality of command signals in response to receipt of the actuation signal according to a first control state and a second control state. The plurality of command signals can be configured to control a surgical robot can include an electromechanical arm, an electromechanical tool mounted to the electromechanical arm including an instrument shaft, and an end effector formed on the instrument shaft configured to perform a plurality of surgical functions on tissue of a patient. In the first control state, a movement of the user interface device in a first selected direction effects a corresponding movement of the end effector in the first selected direction. In the second control state, a movement of the user interface device in the first selected direction does not effect a corresponding movement of the end effector in the first selected movement direction and the end effector can be capable of performing a second surgical function in response to receipt of a second surgical function input by the user interface device. The method can further include entering, by the computing device, the second control state from the first control state in response to receipt of a first transition input by the user interface device.

In some embodiments, one or more of the following features can be optionally included in the system. For example, the method can include storing, by the computing device, a first position representing a position of the user interface device with respect to the first selected direction at the time the second control state is entered, and entering, by the computing device, the first control state from the second control state when a second transition input is received by the user interface device and a current position of the user interface device with respect to the first selected direction is within a tolerance of the stored first position. The method can additionally include, by the computing device, generating a graphical representation of an estimated end effector position according the actuation signal that suitable for overlay upon an image of a current end effector position. In the first control state, movement of the end effector corresponds to movement of the user interface device in any direction. The computing device is configured to control movements and surgical functions of the end effector according to a third control state in response to receipt of a third transition input by the user interface device, and, in the third control state, movement of the user interface device in a second selected direction, different from the first selected direction, does not result in a corresponding movement of the end effector in the second selected direction and the end effector performs a third surgical function, different from the second surgical function, in response to receipt of a third surgical function input by the user interface device. The plurality of command signals prohibit entry of the third control state from the second control state prior to performance of the second surgical function. The computing device can be further configured to: store a second position representing a position of the user interface device with respect to the second selected direction at the time the third control state is entered from the second control state and enter the second control state from the third control state when a fourth transition input is received by the user interface device and a current position of the user interface device with respect to the second selected direction is within a tolerance of the stored second position. The third surgical function can include at least two sequentially performed surgical functions and the plurality of command signals prohibit entry of the second control state from the third control state until each of the at least two surgical functions of the third surgical function is performed. The first surgical function can include clamping the tissue and the second surgical function can include deploying a plurality of staples to the tissue. The plurality of command signals can prohibit entry of the first control state from the third control state. The second transition input, the third transition input, and the fourth transition input can include modulation of the first transition input.

BRIEF DESCRIPTION OF THE DRAWINGS

The invention will be more fully understood from the following detailed description taken in conjunction with the accompanying drawings, in which:

FIG. 1 is a perspective view of one embodiment of a surgical robotic system that includes a user-side portion and a patient-side portion including robotic arms and an electromechanical tool;

FIGS. 5B-5D are perspective views of the tool of FIG. 5A illustrating rotation of an end effector of the electromechanical tool; (B) roll rotation about a y-axis; (C) yaw rotation about a z-axis; (D) combined roll and yaw rotation;

DETAILED DESCRIPTION

Figure 3:
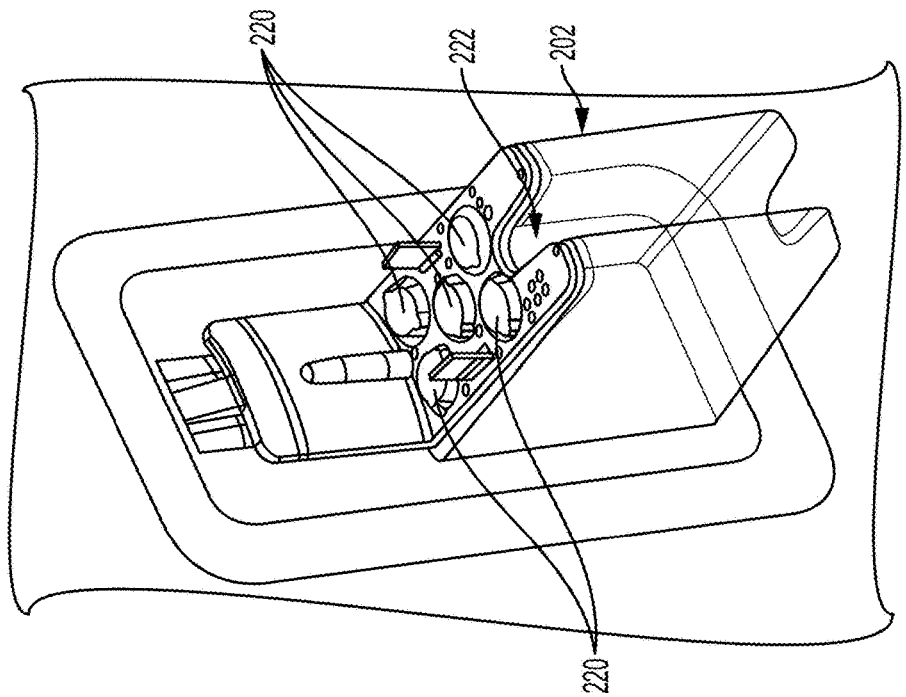
FIG. 3 is a perspective view of a tool driver of the robotic arm of FIG. 2.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Additionally, International Patent Publication No. WO 2014/151621, filed on Mar. 13, 2014, and entitled "Hyperdexterous Surgical System" is incorporated herein by reference.

In general, robotic surgical systems typically include a plurality of electromechanical components including an end effector configured to perform surgical functions on a tissue of a patient. The plurality of electromechanical components can each include one or more actuators that facilitate movement in one or more selected directions (e.g., translational directions and/or rotational directions) to position the end effector in a desired position. The actuators in each of the electromechanical components are typically moved in response to input from a user (e.g., a surgeon) using a user interface device.

Movements of the user interface device are generally correlated to movement of the end effector, such that given movements of the user interface device are mimicked by the end effector. This manner of control can be problematic, however, for end effectors that perform distinct surgical operations in sequence, such as articulation and surgical functions (e.g., clamping, stapling, cutting, etc.). For example, assume an end effector that functions to clamp tissue. In this context, after a user has employed the user interface device to position the end effector, it is desirable for the end effector to remain stationary while the tissue is clamped to avoid applying unnecessary stress to the tissue. However, when movement of the user interface device is mimicked by the end effector, it is up to the user to inhibit movement of the user interface device to keep the end effector stationary.

Embodiments of the present disclosure relate to robotic surgical systems providing control of an end effector in response to actuation of a user interface device based upon at least two different control states. In each control state, selected movement directions of the user interface device are either coupled to or decoupled from corresponding movements directions of the end effector. Furthermore, in each control state, the end effector is capable of performing one or more surgical functions. A decoupled movement direction is recoupled when the user positions the end effector within a range of the position where motion of the user interface and the end effector were decoupled. This selective coupling facilitates intuitive and simple control of the end effector to perform surgical functions.

Embodiments of the disclosure further provide a vision system configured to facilitate recoupling of decoupled movement directions. For example, the vision system can display a current position of the end effector and a graphical representation of the position of the end effector if the decoupled movement direction were recoupled. As the user interface device is moved, the graphical representation is updated with respect to the current end effector position. In this manner, the graphical representation can assist the user in moving the user interface within the appropriate range to recouple the end effector and the user interface device.

Robotic Surgical Systems

The systems, devices, and methods disclosed herein can be implemented using a robotic surgical system.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or portions of the system can be in wired communication and other portions of the system can be in wireless communication.

FIG. 1 is a perspective view of one embodiment of a surgical robotic system 100 that includes a patient-side portion 102 that is positioned adjacent to a patient 104, and a user-side portion 106 that is located a distance from the patient 104, either in the same room and/or in a remote location. The patient-side portion 102 generally includes one or more robotic arms 110 and one or more tool assemblies 112 that are configured to releasably couple to a robotic arm 110. The user-side portion 106 generally includes a vision system 114 for viewing the patient 104 and/or surgical site being operated on and a control system 116 for controlling the movement of the robotic arms 110 and each tool assembly 112 during a surgical procedure.

The control system 116 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console is located in the operating room, and a separate console is located in a remote location. The control system 116 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 116 can also include one or more manually-operated input devices, such as a joystick, exoskeletal glove, a powered and gravity-compensated manipulator, or the like. The one or more input devices can control tele-operated motors which, in turn, control the movement of the surgical system, including the robotic arms 110 and tool assemblies 112. Further embodiments of the control system 116 can include a user interface device 600 and a computer system 900, discussed in greater detail below.

The patient-side portion 102 can have a variety of configurations. As illustrated in FIG. 1, the patient-side portion 102 can couple to an operating table 118. However, in other embodiments, the patient-side portion 102 can be mounted to a wall, to the ceiling, to the floor, or to other operating room equipment. Further, while the patient-side portion 102 is shown as including two robotic arms 110, more or fewer robotic arms 110 may be included. Furthermore, the patient-side portion 102 can include separate robotic arms 110 mounted in various positions, such as relative to the operating table 118 (as shown in FIG. 1). Alternatively, the patient-side portion 102 can include a single assembly that includes one or more robotic arms 110 extending therefrom.

Figure 2:
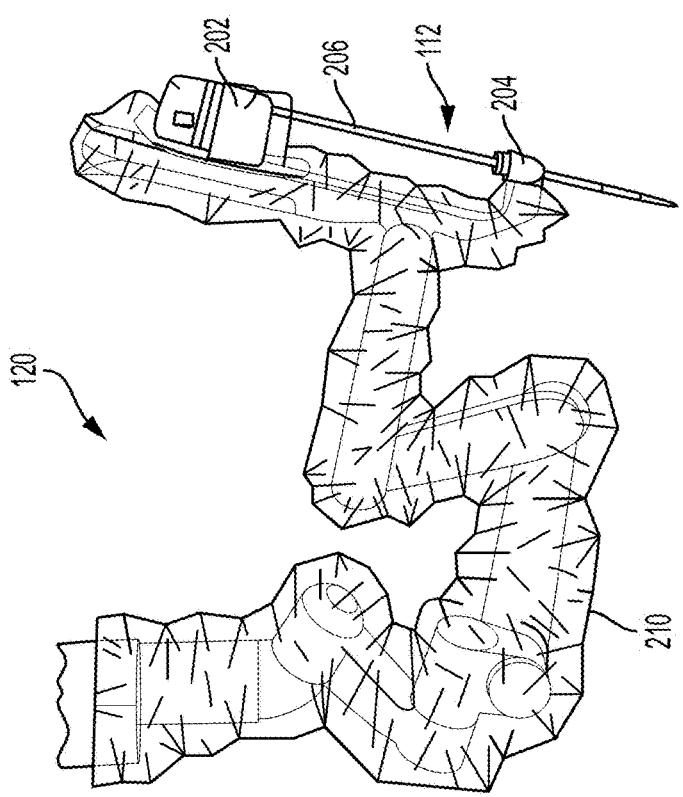
FIG. 2 is a perspective view of one embodiment of a robotic arm with the electromechanical tool of FIG. 1 releasably and replaceably coupled to the robotic arm.
Figure 4:
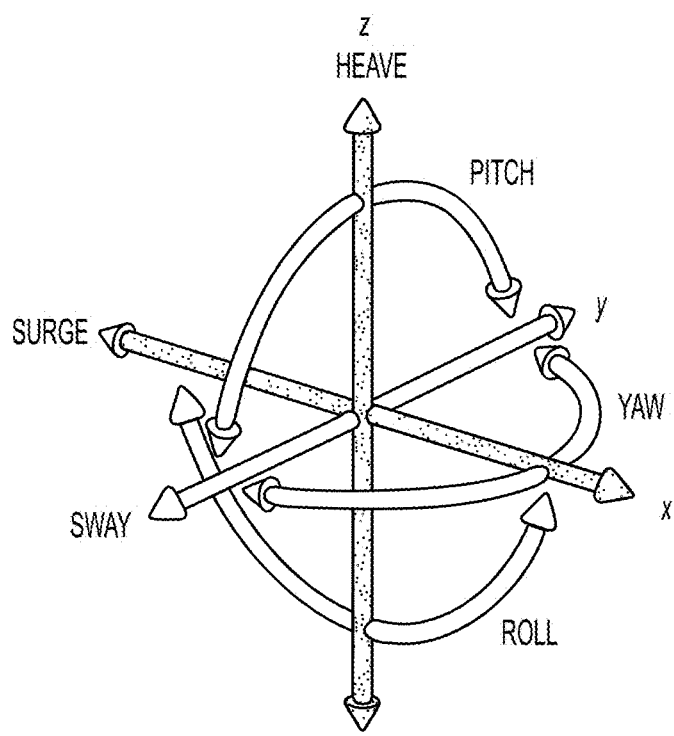
FIG. 4 is a graphical representation of terminology associated with six degrees of freedom.

FIG. 2 illustrates another embodiment of a robotic arm 120 and the tool assembly 112 of FIG. 1 releasably and replaceably coupled to the robotic arm 110. Other surgical instruments can instead be coupled to the robotic arms 110, as discussed herein. The robotic arm 120 is configured to support and move the associated tool assemblies 112 along one or more degrees of freedom. For example, FIG. 4 illustrates degrees of freedom of a coordinate system represented by three translational variables with respect to orthogonal axes (e.g., x, y, and z) and three rotational variables about each of the orthogonal axes (e.g., Euler angles). Together, these six variables can be employed to describe the position of a component of a surgical system with respect to a given reference Cartesian frame. With respect to translation, the term "surge" refers to movement parallel to the x-axis (e.g., forward into the page and backward out of the page), the term "sway" refers to movement parallel to the y-axis (e.g., left and right within the page), and the term "heave" refers to movement parallel to the z-axis (e.g., up and down within the page). With regard to rotation, "roll" refers to rotation about the x-axis (e.g., tilting side to side), "roll" refers to rotation about the y-axis (e.g., tilting forward and backward), and "yaw" refers to rotation about the z-axis (e.g., turning left and right).

The robotic arm 120 can include a tool driver 202 at a distal end of the robotic arm 120, which can assist with controlling features associated with the tool assembly 112. The robotic arm 120 can also include an entry guide 204 (e.g., a cannula mount, cannula, etc.) that is a part of or releasably and replaceably coupled to the robotic arm 120, as shown in FIG. 2. A shaft 206 of the tool assembly 112 can be inserted through the entry guide 204 for insertion into a patient, as shown in FIG. 2 in which the shaft 206 of the tool assembly 112 of FIG. 1 is shown inserted through the entry guide 204.

In order to provide a sterile operation area while using the surgical system, a barrier 210 can be placed between the actuating portion of the surgical system (e.g., the robotic arm 120) and the surgical instruments coupled thereto (e.g., the tool assembly 112, etc.). A sterile component, such as an instrument sterile adapter (ISA), can also be placed at the connecting interface between the tool assembly 112 and the robotic arm 120. The placement of an ISA between the tool assembly 112 and the robotic arm 120 can ensure a sterile coupling point for the tool assembly 112 and the robotic arm 120. This permits removal of surgical instruments from the robotic arm 120 to exchange with other surgical instruments during the course of a surgery without compromising the sterile surgical field.

FIG. 3 illustrates the tool driver 202 in more detail. As shown, the tool driver 202 includes one or more motors (e.g., five motors 220), that control a variety of movements and actions associated with the tool assembly 112 coupled to the robotic arm 120. For example, each motor 220 can couple to and/or interact with an activation feature (e.g., gear) associated with the tool assembly 112 for controlling one or more actions and movements that can be performed by the tool assembly 112, such as for assisting with performing a surgical operation. The motors 220 are accessible on the upper surface of the tool driver 202, and thus the tool assembly 112 is configured to mount on top of the tool driver 202 to couple thereto. Exemplary embodiments of motor operation and components of the tool assembly 112 configured to be controlled by tool driver motors 220 are further described in International Patent Publication No. WO 2014/151952 entitled "Compact Robotic Wrist," filed on Mar. 13, 2014, and International Patent Publication No. WO 2014/151621 entitled "Hyperdexterous Surgical System," filed on Mar. 13, 2014, and in U.S. patent application Ser. No. 15/237,653 entitled "Methods, Systems, And Devices For Controlling A Motor Of A Robotic Surgical Systems," filed on Aug. 16, 2016, each of which is hereby incorporated by reference in its entirety.

The tool driver 202 also includes a shaft-receiving channel 222 formed in a sidewall thereof for receiving the shaft 206 of the tool assembly 112. In other embodiments, the shaft 206 can extend through an opening in the tool driver 202, or the two components can mate in various other configurations.

Figure 5A:
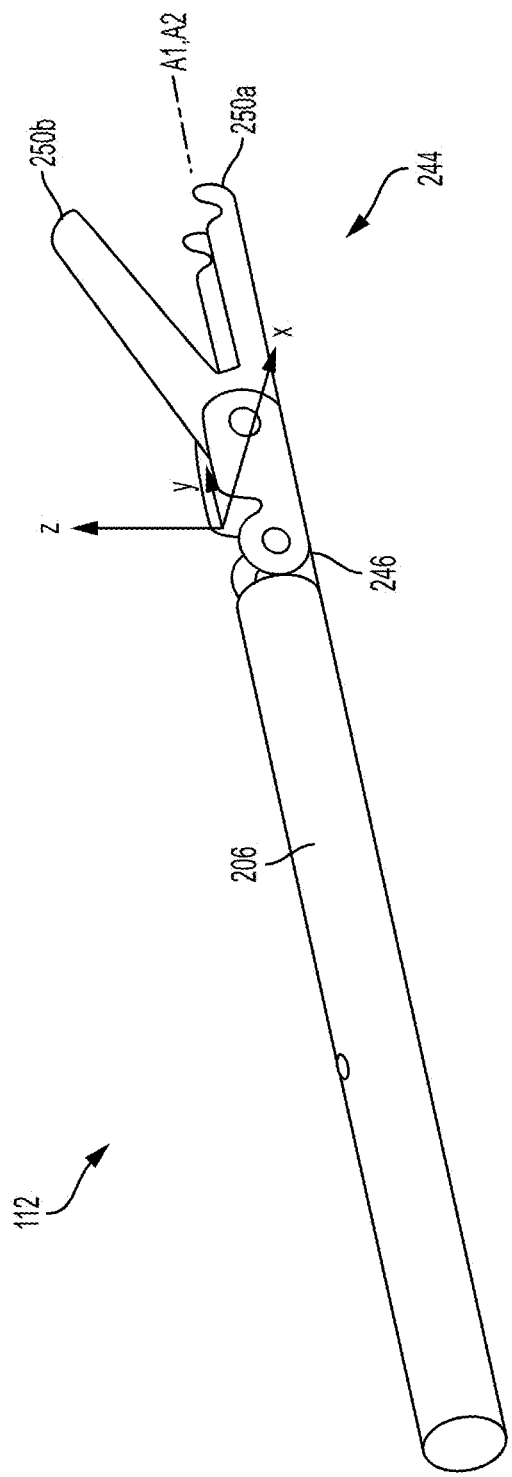
FIG. 5A is a perspective view of an embodiment of a portion of the electromechanical tool of FIG. 1.

FIG. 5A illustrates one embodiment of a portion of a tool assembly 112 that includes the elongated shaft 206, an end effector 244, and a wrist 246 that couples the end effector 244 to the shaft 206 at a distal end of the shaft 206. The end effector 244 is configured to move relative to the shaft 206 at the wrist 246 (e.g., by pivoting at the wrist 246) to position the end effector 244 at a desired location relative to a surgical site during use of the tool assembly 112. In at least some embodiments, the shaft 206, and hence the end effector 244 coupled thereto, is configured to rotate about a longitudinal axis A1 of the shaft 206. In such embodiments, the various components of the tool driver 202 are configured to control the rotational movement of the shaft 206. Each of the shaft 206, the end effector 244, and wrist the 246 are discussed further below.

The tool assembly 112 can have any of a variety of configurations. In general, the tool assembly 112 can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The tool assembly 112 in at least some embodiments is configured to apply energy (e.g., radiofrequency (RF) energy and/or ultrasonic energy) to tissue, while in other embodiments the tool assembly 112 is not configured to apply energy to tissue.

The shaft 206 can have any of a variety of configurations. In general, the shaft 206 is an elongate member extending distally from the tool driver 202 and has at least one inner lumen extending therethrough. The shaft 206 is fixed to the tool driver 202, but in other embodiment the shaft 206 can be releasably coupled to the tool driver 202 such that the shaft 206 can be interchangeable with other shafts. This may allow a single tool driver 202 to be adaptable to various shafts having different end effectors.

The end effector 244 can have a variety of sizes, shapes, and configurations. The end effector 244 includes a tissue grasper having a pair of opposed jaws 250a, 250b configured to move between open and closed positions with one or both of the jaws 250a, 250b configured to pivot at the wrist 246 to move the end effector 244 between the open and closed positions. The end effector 244 in other embodiments can have other configurations, e.g., scissors, a babcock, a retractor, etc.

The wrist 246 can have any of a variety of configurations. Exemplary embodiments of a wrist 246 of a tool assembly 112 and of effecting articulation at the wrist 246 are described in International Patent Publication No. WO 2014/151952 entitled "Compact Robotic Wrist," filed on Mar. 13, 2014, International Patent Publication No. WO 2014/151621 entitled "Hyperdexterous Surgical System," filed on Mar. 13, 2014, U.S. patent application Ser. No. 15/200,283 entitled "Methods, Systems, And Devices For Initializing A Surgical Tool," filed on Jul. 1, 2016, and U.S. patent application Ser. No. 15/237,648 entitled "Methods, Systems, And Devices For Causing End Effector Motion With A Robotic Surgical System," filed on Aug. 16, 2016, each of which are hereby incorporated by reference in their entireties.

In general, the wrist 246 can include a joint configured to allow movement of the end effector 244 relative to the shaft 206. For example, the wrist 246 can include a pivot joint at which the jaws 250a, 250b are pivotally attached. In some embodiments, the pivoting motion can include pitch movement about a first axis of the wrist 246 (e.g., the x-axis), yaw movement about a second axis of the wrist 16 (e.g., the z-axis), and combinations thereof, to allow for 360° rotational movement of the end effector 244 about the wrist 246. In other embodiments, the pivoting motion can be limited to movement in a single plane, e.g., only pitch movement about the first axis of the wrist 246 or only yaw movement about the second axis of the wrist 246, such that end effector 244 rotates in a single plane.

In the illustrated embodiments of FIGS. 5A-5D, movement of the end effector 244 can occur between an unarticulated position of the end effector 244 and various articulated positions of the end effector 244. In the unarticulated position (FIG. 5A), the end effector 244 is substantially longitudinally aligned with the shaft 206. For example, a longitudinal axis A2 of the end effector 244 is substantially aligned with a longitudinal axis A1 of the shaft 206 such that the end effector 244 is at a substantially zero angle relative to the shaft 206. In an articulated position, the end effector 244 is angularly orientated relative to the shaft 206. For example, the longitudinal axis A2 of the end effector 14 can be angled relative to the longitudinal axis A1 of the shaft 206 by rotation (e.g., about the z-axis) such that the end effector 244 is at a non-zero angle relative to the shaft 206, as illustrated in FIG. 5B. A person skilled in the art will appreciate that the end effector 244 may not be precisely aligned with the shaft 206 in the unarticulated position (e.g., may not be at a precise zero angle relative thereto) but nevertheless be considered to be aligned with the shaft 206 (e.g., be at a substantially zero angle) due to any number of factors, such as manufacturing tolerance and precision of measurement devices.

In further embodiments, movement of the end effector 244 can also include rotational movement of the end effector 244 about its longitudinal axis A2 (e.g., about the y-axis), alone or in combination with rotation about the x- or z-axes. As an example, FIG. 5C illustrates movement of the end effector 244 arising from rotation of the shaft 206 about its longitudinal axis A1. As a further example, FIG. 5D illustrates movement of the end effector 244 arising from a combination of rotational movement about the y-axis and the z-axis.

Control System

Figure 6:
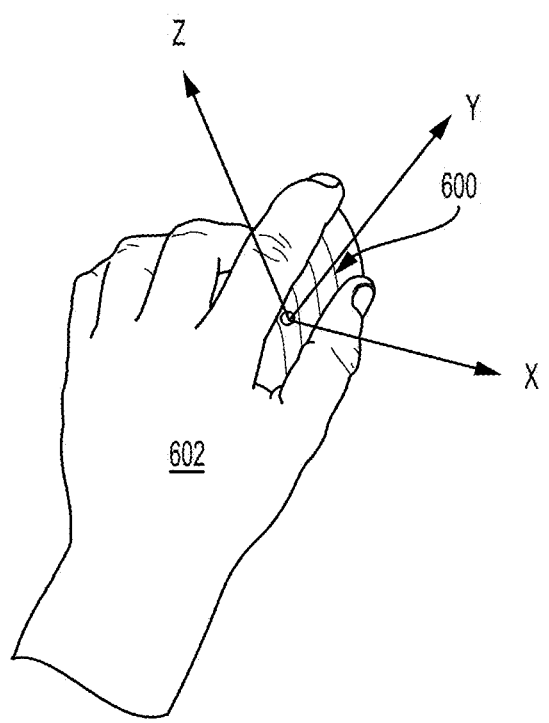
FIG. 6 is a perspective view of a user interface device (UID) held within a user's hand.

Embodiments of the control system 116 employ a user interface device 600 and computer system 900 to control of movements and surgical functions of the end effector 244. An embodiment of the user interface device 600 is illustrated in FIG. 6. The user interface device 600 is a manually-operated input device configured for hand-held actuation by a user (e.g., a surgeon). For example, the user interface device 600 is dimensioned for receipt within a user's hand 602 and includes a plurality of sensors (not shown) capable of measuring one or more translation and rotation movements of the user interface device 600. In additional embodiments, the user interface device 600 include a plurality of user interface objects (e.g., switches, buttons, knobs, etc.; not shown) capable of registering actuation of the user interface device 600 other than movement. In further embodiments, the user interface device 600 include one or more additional devices capable of registering a user actuation other than movement of the user interface device 600 (e.g., a foot pedal). Exemplary embodiments of the user interface device 600 are further described in U.S. Provisional Patent Application No. 62/236,356, filed on Oct. 2, 2015 and entitled. "User Input Device (UID) and Guided User Interface (GUI) for a Robotic Surgical System," U.S. patent application Ser. No. 15/282,243 entitled, "User Input Device for Robotic Surgical System," filed on Sep. 30, 2016, and U.S. patent application Ser. No. 15/282,353 entitled "System and Method of Converting User Input into Motion of a Surgical Instrument via a Robotic Surgical System," filed on Sep. 30, 2016, each of which is hereby incorporated by reference in its entirety. In response to user actuation, the user interface device 600 generates a plurality of actuation signals. The computer system 900 receives the plurality of actuation signals and, in response, generates a plurality of command signals for control of the robotic arms 110 and the tool assembly 112 in order to articulate and perform surgical functions with the end effector 244.

In general, existing techniques and systems for motion control of the end effector 244 using the user interface device 600 are configured to map movements of the user interface device 600 onto movements of the end effector 244. That is to say, each movement of the user interface device 600 is mimicked by the end effector 244. However, this manner of control can create problems when employed to control tool assemblies 112 that perform various tasks sequentially (e.g., movement, followed by one or more surgical functions such as clamping, stapling, or cutting, followed again by movement). Notably, it can be challenging for a user to actuate the user interface device 600 to cause the end effector 244 to perform surgical functions without also moving the user interface device 600 and unintentionally causing the end effector 244 to move.

Motion control systems have also been developed for robotic surgical systems that remove motion control of the end effector 244 from the user interface device 600 at the user's discretion. However, when motion control of the end effector 244 is restored to the user interface device 600, the end effector 244 will move to the position corresponding to the position of the user interface device 600. Thus, if the position of the user interface device 600 is changed while motion control of the end effector 244 by the user interface device 600 is removed, the position of the end effector 244 will change as well once motion control of the end effector 244 by the user interface device 600 is restored. Such motions occur near instantaneously (e.g., discontinuously) and can potentially damage tissue. Furthermore, such control systems do not allow the user to remove control of the end effector 244 movement from movement of the user interface device 600 in less than all directions.

These problems are addressed by embodiments of the control system 116 disclosed herein. As discussed in detail below, the computer system 900 is configured to control movement and a plurality of surgical functions performed by the end effector 244 in response to actuation of the user interface device 600 based upon two or more control states. In general, actuation signals received by the user interface device 600 are interpreted differently in each control state to control movement and surgical functions of the end effector 244.

With respect to movement, embodiments of the control system 116 either couple or decouple movement of the user interface device 600 to movement of the end effector 244 in each movement direction in a control state. When movement of the user interface device 600 and the end effector 244 are coupled in a selected direction, a movement of the user interface device 600 in the selected direction effects a corresponding movement of the end effector 244 in the selected direction. Conversely, when movement of the user interface device 600 and the end effector 244 are decoupled in a selected direction, a movement of the user interface device 600 in the selected direction does not effect a corresponding movement of the end effector 244 in the selected directions.

With respect to surgical functions, embodiments of the control system 116 also associate control of the surgical functions with a control state. That is, certain surgical functions can only be performed when the control system 116 operates in the control state associated with such surgical functions and receives a corresponding surgical function input. Thus, when the control system 116 operates in a control state not associated with a given surgical function, the end effector 244 does not receive a command to perform that surgical function, even if such a surgical function input is provided. Examples of surgical functions can include, but are not limited to, physically grabbing tissue, causing objects (e.g., pins, needles, staples, etc.) to penetrate tissue, application of suction to tissue, delivery of flowable compounds to tissue (e.g., adhesives, cooling or heating compounds, etc.) or any other surgical functions performed by end effectors 244. Embodiments of the surgical function inputs can include, but are not limited to, actuation of one or more user interface objects and actuation of another device in communication with the user interface device 600 (e.g., a foot pedal), and the like.

In an embodiment, the control system 116 is configured to allow the user to control transition between control states. In one aspect, the control system 116 allows a user to transition between one control state in which movement in a selected direction is coupled and another control state in which the movement in the selected direction is decoupled. This transition is alternatively referred to as a decoupling transition. For example, the user can cause a decoupling transition to occur by providing a transition input to the user interface device 600. This transition input can be configured as a relatively simple actuation of the user interface device 600, facilitating ease of use of the control system 116. For example, embodiments of transition inputs suitable for effecting a decoupling transition can include, but are not limited to, one or more of actuating a user interface object of the user interface device 600 (e.g., actuating a button or flipping a switch) and application of varying pressure to the user interface device 600 (e.g., squeezing).

In another aspect, the control system 116 allows a user to perform a reverse transition, from a control state in which a selected movement direction is decoupled and another control state in which the selected movement direction is recoupled. This transition is alternatively referred to as a recoupling transition. Embodiments of the control system 116 are configured to perform recoupling transitions only when two conditions are satisfied. In an embodiment of the control system 116, the first condition is satisfied when the user actuates a selected user interface object of the user interface device 600, and the second condition is satisfied when the user positions the user interface device 600 within a coupling range (e.g., linear and angular direction and position as well as rotational direction and position), with respect to the selected movement direction, as when the selected movement direction was decoupled. In one example the coupling range can be +/− about 5 mm, or +/− about 7° for rotational movement.

The requirement that two conditions are satisfied before performing a recoupling transition reflects a heightened caution to avoid the potentially harmful effects that can arise from discontinuous movements of the end effector 244 during a recoupling transition. In certain embodiments, the control system 116 is configured to perform a recoupling transition when these two conditions are satisfied simultaneously. In alternative embodiments, the control system 116 is configured to perform a recoupling transition when the first and second conditions are performed sequentially.

Figure 8:
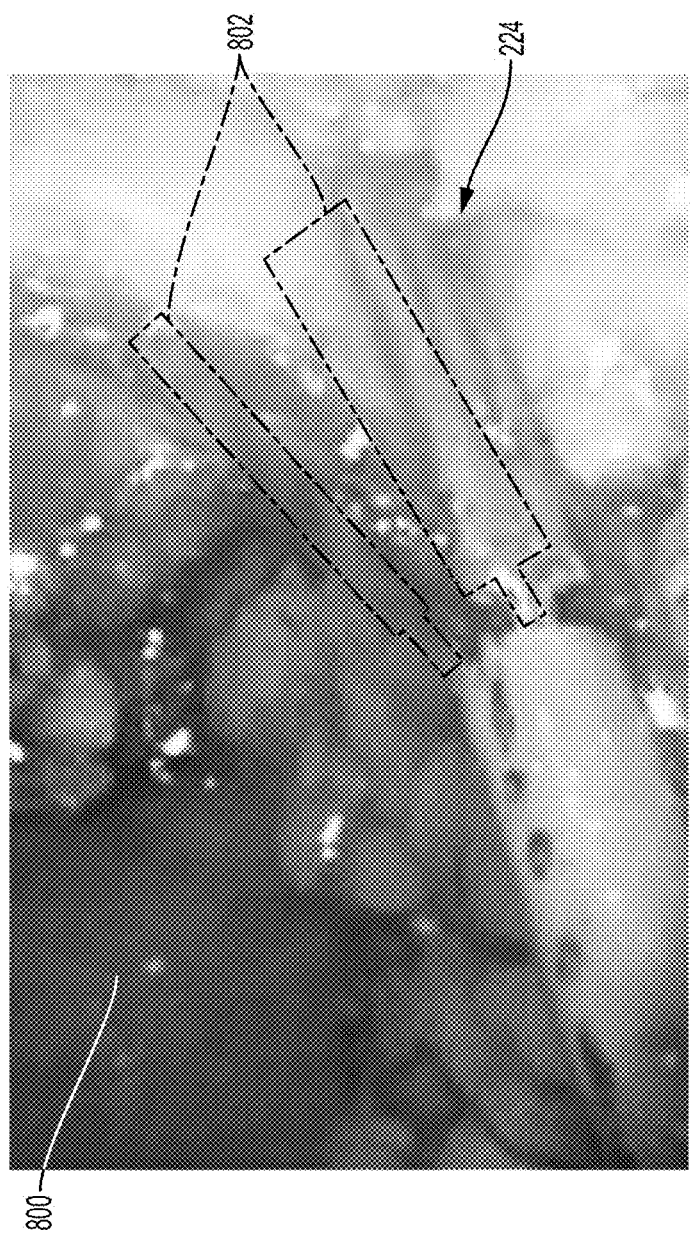
FIG. 8 is a graphical representation of a display of a vision system of the surgical robotic system of FIG. 1 illustrating a camera view of an end effector of the tool of FIG. 5A.

Recognizing the potential difficulty that a user can encounter when attempting to position the user interface device 600 to satisfy the second condition and effect a recoupling transition, embodiments of the control system 116 are also configured to communicate with the vision system 114 to provide a user with real-time, visual assistance. For example, as illustrated in FIG. 8, the vision system 114 receives and displays real-time images 800 of the position of the end effector 244 within the patient's body (e.g., video from a camera attached to an endoscope or the end effector 244). Accordingly, when a user provides a transition input to effect a recoupling transition, the computer system 900 generates a graphical image 802 for display by the vision system 114. The graphical image 802 represents an estimate of the position that the end effector 244 would adopt, based upon a current position of the user interface device 600, if the decoupled movement direction was recoupled. By overlaying the graphical image 802 upon the real-time images 800, a user can see the relative position of the end effector 244 and the position of the end effector 244 that would be adopted according to the current position of the user interface device 600, providing guidance for positioning the user interface device 600 within the coupling range.

In further embodiments, control state transitions are state dependent. That is, allowable state transitions depend upon the manner in which a current control state was achieved. When the control system 116 is configured to provide three or more control states, different movement directions are coupled or decoupled in each of the respective control states. Thus, to ensure continuity of motion, it is important that the control system 116 only allow the user to perform recoupling transitions in a particular order with respect to the corresponding coupling transitions. As an example, assume that the control system 116 is configured to provide three control states, where a second control state is entered from a first control state and a third control state is entered from the second control state. The control system 116 prohibits transitions directly from the first control state to the third control state, or the third control state to the first control state. Instead, an intervening transition to the second control state is required.

In other examples, whether a given control state transition is permitted depends upon performance of surgical functions. In one example, the control system 116 is configured to prohibit a transition between two control states until one or more selected surgical function is performed. In another aspect, the control system 116 is configured to prohibit a transition between two control states while a surgical function is being performed.

Figure 7A:
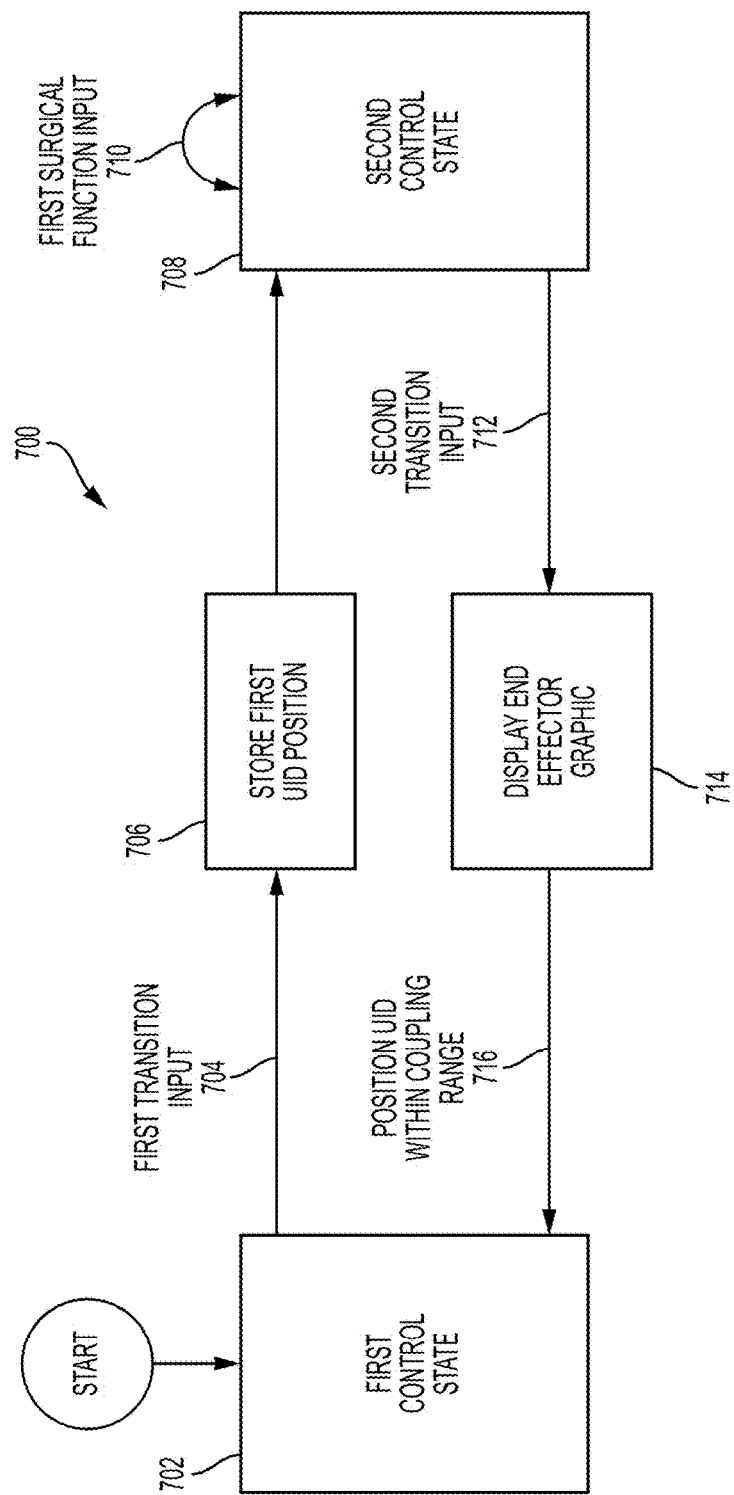
FIG. 7A is a flow diagram illustrating embodiments of control states for controlling movement of the electromechanical tool of FIG. 5A.
Figure 7B:
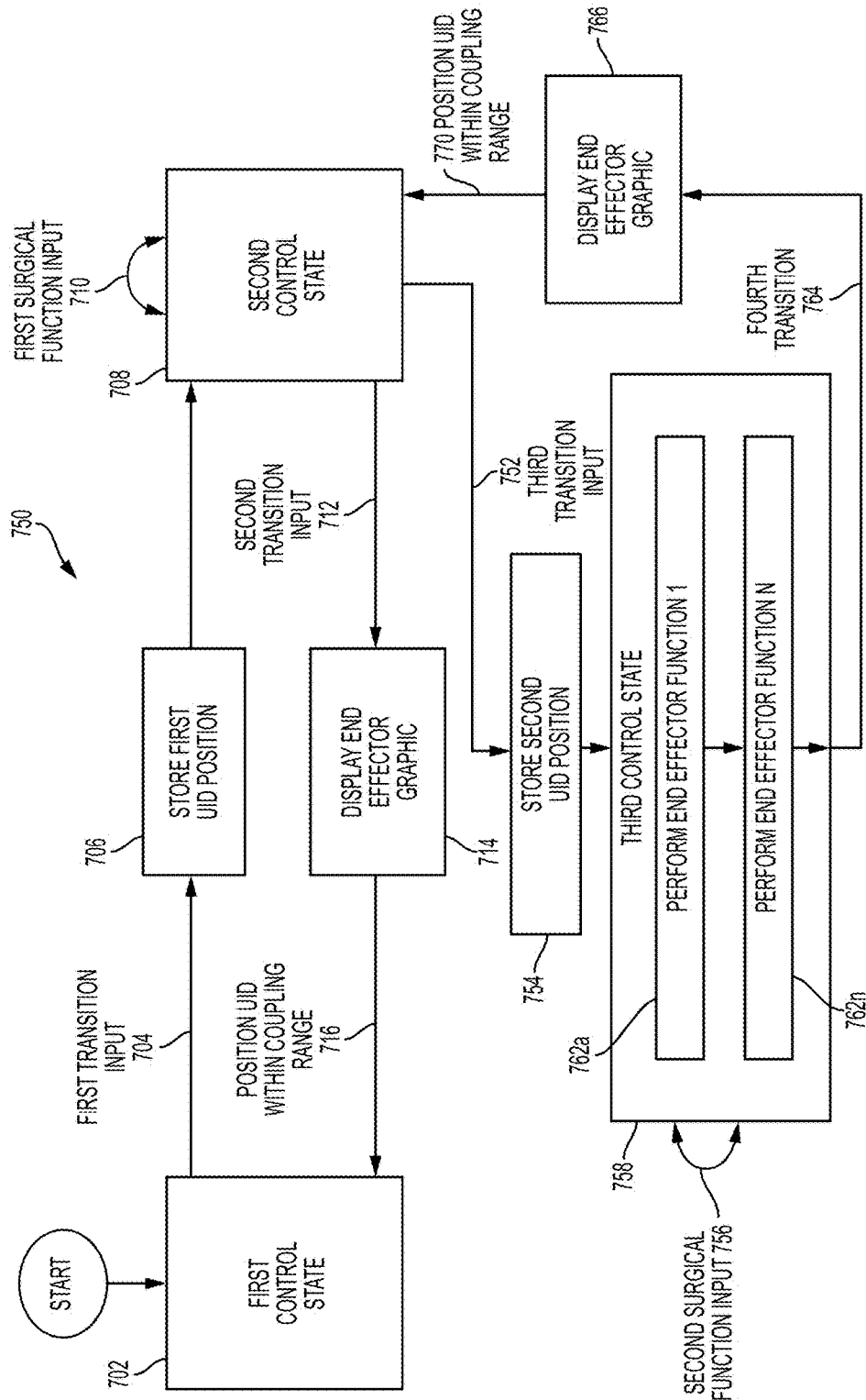
FIG. 7B is a flow diagram illustrating alternative embodiments of control states for controlling movement of the electromechanical tool of FIG. 5A.

FIGS. 7A and 7B illustrate embodiments of methods 700, 750 for controlling movement and surgical functions of the end effector 244 according to at least two control states. In the method 700 of FIG. 7A, a scenario is illustrated, where the end effector 244 is controlled according to two control states, a first control state 702 and a second control state 708. In the method 750 of FIG. 7B, another scenario is illustrated, where the end effector 244 is controlled according to the first control state 702, the second control state 708, and a third control state 758. In the first control state 702, movement of the user interface device 600 in a plurality of selected directions is coupled to movement of the end effector 244, while in the second control state 708, movement of the user interface device 600 in one or more of the selected directions is decoupled from movement of the end effector 244. In the second control state 708, the end effector 244 is further configured to perform a first surgical function in response to receipt of a first surgical function input 610. In the third control state 758, movement of the user interface device 600 is decoupled from movement of the end effector 244 in one or more additional directions, as compared to the second control state 708. The end effector is further configured to perform a plurality of second surgical functions (e.g., 762a, 762b, ... 762n) in the third control state 758. It is understood that in further embodiments of the control system 116 additional control states can be added, where coupling or decoupling of each motion direction and associated surgical functions are independently selected for each control state.

For the purpose of explaining one embodiment, assume that the end effector 244 is a clamp capable of translation in the x-direction, the y-direction, the z-direction, rotation in the yaw direction (about the z-axis), and combinations thereof. Further assume that, in the first control state 702, the position of the end effector 244 is coupled to the position of the user interface device 600 in the x-direction, y-direction, z-direction, and in yaw. In the second control state 708, also assume that the position of the end effector 244 is coupled to the position of the user interface device 600 in the x-direction, the y-direction, and the z-direction, while the yaw direction is decoupled, and that the end effector 244 is capable of performing a clamping surgical function.

In the first control state 702, a user employs the user interface device 600 to position the end effector 244 at a desired location with respect to tissue of the patient in preparation to perform a first surgical function. Since the first surgical function is associated with the second control state 708, not the first control state 702, a decoupling transition from the first control state 702 to the second control state 708 must be accomplished before the first surgical function can be performed.

The decoupling transition from the first control state 702 to the second control state 708 is made upon receipt of a first transition input in operation 704. In an embodiment, the first transition input is application of pressure to the user interface device 600 (e.g., pressure within a first pressure range). As illustrated in operation 706 of FIG. 7A, after the first transition input is received in operation 704, the computer system 900 stores a first position of the user interface device 600. In an embodiment, this stored first position includes at least the position of the user interface device 600 with respect to the direction that is to be decoupled when the second control state 708 is entered. Under the assumed conditions, since the yaw direction is to be decoupled upon entry into the second control state 708 from the first control state 702, the computer system 900 stores at least the yaw direction when the control system 116 enters the second control state 708.

Once the second control state 708 is entered, the end effector 244 performs the first surgical function when a user provides a first surgical function input in operation 710. For example, in an embodiment, the first surgical function input received in operation 710 is actuation of a selected user interface object of the user interface device 600. Actuation of any other user interface object in operation 710 does not constitute the first surgical function input and will not cause the end effector 244 to perform the first surgical function. In an embodiment, the first surgical function input is actuation of a button of the user interface device 600.

To effect a recoupling transition returning the control system 116 to the first control state 702 from the second control state 708, a user must satisfy a set of first and second conditions. The first condition is satisfied by providing a second transition input in operation 712. In an embodiment, the second transition input is release of the pressure applied to the user interface device 600 (e.g., the opposite of the first transition input). While this example discusses return to the first control state 702 from the second control state 708 after the first surgical function is performed, it is understood that a user can return to the first control state 702 from the second control state 708 without performing the first surgical function.

To help a user satisfy the second condition and effect the recoupling transition, after receipt of the second transition input, the computer system 900 generates the graphical image 802 (FIG. 8) and transmits the graphical image 802 for display by the vision system 114 in operation 714. The graphical image 802 is based upon the current position of the user interface device 600 and is updated in real-time as the user interface device 600 is moved. Concurrently, in operation 716, the current position of the user interface device 600 is compared to the former position of the user interface device 600 stored in operation 706 with respect to the decoupled direction (e.g., the yaw-direction). Once a user adjusts the position of the user interface device 600 with respect to the selected direction (e.g., the yaw-direction) within the coupling range, the first control state 702 is reentered.

In the method 750 of FIG. 7B, a third control state 758 is added as compared to the method 700 of FIG. 7A. The first control state 702 and the second control state 708 are as discussed above, unless otherwise indicated below. In the third control state 758, movement of the user interface device 600 in one or more selected directions is decoupled from movement of the end effector 244. For example, since the yaw-direction is already decoupled in the second control state 708, the movement direction decoupled in the third control state 758 is selected from one or more of the x-direction, the y-direction, and the z-direction. In the third control state, the end effector 244 is further configured to perform a plurality of second surgical functions in operations 762a, 762b, ... 762n in response to receipt of a second surgical function input 654.

For the purpose of illustration, assume that the end effector 244 is decoupled from each of the x-direction, y-direction, and z-direction in the third control state 758. Further assume that the end effector is capable of performing a plurality of second surgical functions such as stapling 762a and cutting 762b in the third control state 758.

As discussed above, a decoupling transition from the first control state 702 to the second control state 708 is performed according to operations 704-706. From the second control state 708, a user can choose from three different sets of actions. In one set of actions, a recoupling transition to the first control state 702 is performed according to operations 712-716, without performing the first surgical function. In a second set of actions, the first surgical function is performed, followed by a recoupling transition to the first control state 702. In a third set of actions, a further decoupling transition to the third control state 758 can be performed. To transition to the third control state 758 from the second control state 708, a user provides a third transition input in operation 752. In an embodiment, the third transition input received in operation 752 is the further application of pressure to the user interface device 600 within a second pressure range, higher than the first pressure range.

As illustrated in FIG. 7B, after the third transition input is received in operation 752, the computer system 900 stores a second position of the user interface device 600 in operation 754. In an embodiment, this stored second position includes at least the position of the user interface device 600 with respect to the direction(s) that are to be decoupled when the third control state 758 is entered. Under the assumed conditions of the third control state 758, since each of the x-direction, the y-direction, and the z-direction are to be decoupled upon entry into the third control state 758 from the second control state 708, the computer system 900 stores each x-direction, the y-direction, and the z-direction as the second position of the user interface device 600.

Once the third control state 758 is entered, the end effector 244 is capable of performing the plurality of second surgical functions when a user provides a second surgical function input in operation 756. For example, in an embodiment, the second surgical function input received in operation 756 is actuation of a selected user interface object of the user interface device 600. Actuation of any other user interface object in operation 756 does not constitute the second surgical function input and will not cause the end effector 244 to perform the plurality of second surgical function. In an embodiment, the first surgical function input is actuation of a foot pedal in communication with the user interface device 600 and the plurality of second surgical functions are performed sequentially (e.g., a stapling surgical function in operation 762a, followed by a cutting surgical function in operation 762b).

To return to the second control state 708 from the third control state 758, a user must satisfy another set of first and second conditions to effect a recoupling transition. In this case, the first condition is satisfied by providing a fourth transition input in operation 764. In an embodiment, the fourth transition input is release of pressure applied to the user interface device 600 (e.g., decreasing the applied pressure from a pressure within the second pressure range to a pressure within the first pressure range; the opposite of the third transition input). While this example discusses return to the second control state 708 from the third control state 758 after the second surgical function is performed, it may be understood that a user can return to the second control state 708 from the third control state 758 without performing the second surgical function in operations 762a-762n.

The control system 116 also helps a user satisfy the second condition for return to the second control state 708 from the third control state 758. After receipt of the fourth transition input in operation 764, the computer system 900 generates the graphical image 802 and transmits the graphical image 802 (FIG. 8) for display by the vision system 114 in operation 766. The graphical image 802 is based upon the current position of the user interface device 600 and is updated in real-time as the user interface device 600 is moved. Concurrently, in operation 770, the current position of the user interface device 600 is compared to the former position of the user interface device stored in operation 752 with respect to the decoupled direction (e.g., the x-direction, the y-direction, and the z-direction). Once a user adjusts the position of the user interface device 600 with respect to the selected the x-direction, the y-direction, and the z-direction within respective the coupling ranges in each direction, the second control state 708 is reentered.

In an embodiment, the second transition input received in operation 712, the third transition input received in operation 752, and the fourth transition input received in operation 764 are each modulation of the first transition input received in operation 704 (e.g., varying a pressure applied to the user interface device 600). However, alternative embodiments of each transition input can be configured differently.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to a user and a keyboard and a pointing device, e.g., a mouse, a trackball, etc., by which a user may provide input to the computer. Other kinds of devices can be used to provide for interaction with a user as well. For example, feedback provided to a user can be any form of sensory feedback, such as for example visual feedback, auditory feedback, or tactile feedback; and input from a user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 9:
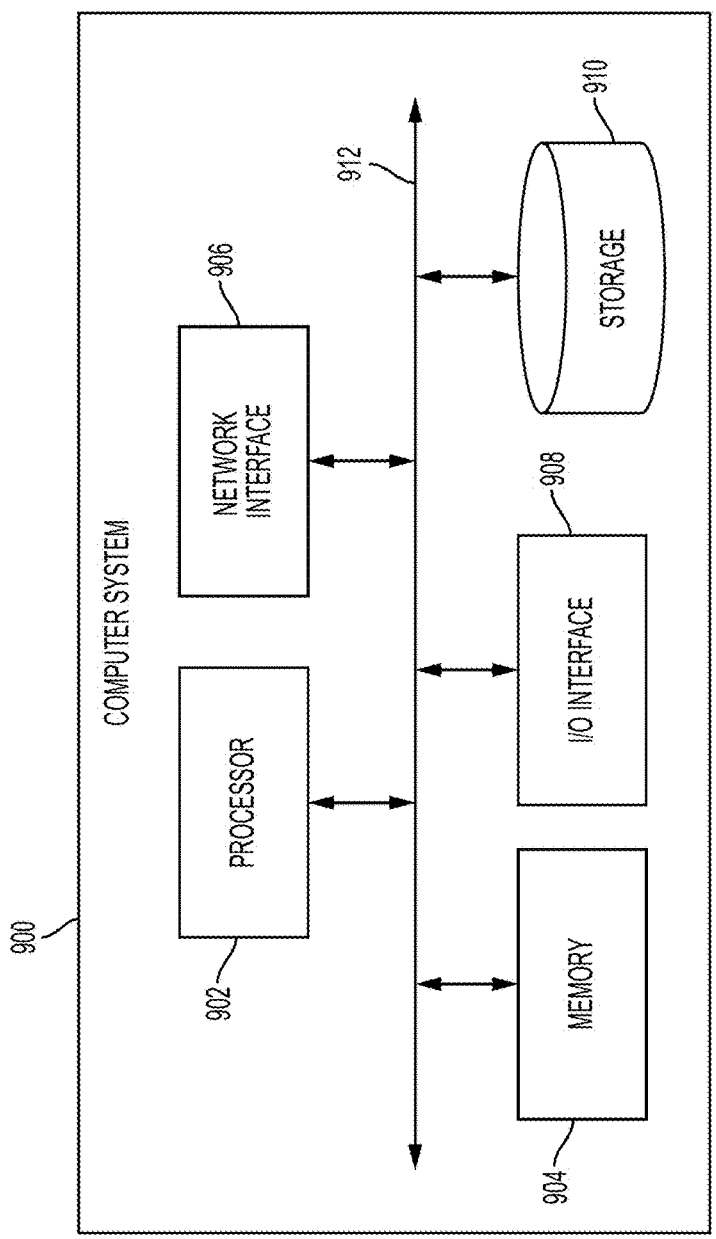
FIG. 9 is a schematic illustration of a computer system configured to generate a plurality of command signals for controlling movement of the electromechanical tool of FIG. 5A from based upon movement of the user interface device of FIG. 6.

FIG. 9 illustrates an exemplary embodiment of a computer system 900. As shown, the computer system 900 includes one or more processors 902 which can control the operation of the computer system 900. "Processors" are also referred to herein as "controllers." The processor(s) 902 can include any type of microprocessor or central processing unit (CPU), including programmable general-purpose or special-purpose microprocessors and/or any one of a variety of proprietary or commercially available single or multi-processor systems. The computer system 900 can also include one or more memories 904, which can provide temporary storage for code to be executed by the processor(s) 902 or for data acquired from one or more users, storage devices, and/or databases. The memory 904 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 900 can be coupled to a bus system 912. The illustrated bus system 912 is an abstraction that represents any one or more separate physical busses, communication lines/interfaces, and/or multi-drop or point-to-point connections, connected by appropriate bridges, adapters, and/or controllers. The computer system 900 can also include one or more network interface(s) 906, one or more input/output (IO) interface(s) 908, and one or more storage device(s) 910.

The network interface(s) 906 can enable the computer system 900 to communicate with remote devices, e.g., other computer systems, over a network, and can be, for non-limiting example, remote desktop connection interfaces, Ethernet adapters, and/or other local area network (LAN) adapters. The IO interface(s) 908 can include one or more interface components to connect the computer system 900 with other electronic equipment. For non-limiting example, the IO interface(s) 908 can include high speed data ports, such as universal serial bus (USB) ports, 1394 ports, Wi-Fi, Bluetooth, etc. Additionally, the computer system 900 can be accessible to a human user, and thus the IO interface(s) 908 can include displays, speakers, keyboards, pointing devices, and/or various other video, audio, or alphanumeric interfaces. The storage device(s) 910 can include any conventional medium for storing data in a non-volatile and/or non-transient manner. The storage device(s) 910 can thus hold data and/or instructions in a persistent state, i.e., the value(s) are retained despite interruption of power to the computer system 900. The storage device(s) 910 can include one or more hard disk drives, flash drives, USB drives, optical drives, various media cards, diskettes, compact discs, and/or any combination thereof and can be directly connected to the computer system 900 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 9 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 900 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 900 can also include a web server for generating and/or delivering the web pages to client computer systems.

In an exemplary embodiment, the computer system 900 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   an electromechanical tool including an instrument shaft and an end effector formed on the instrument shaft, wherein the end effector is configured to perform a plurality of surgical functions on tissue of a patient;
   an electromechanical arm configured for movement with respect to multiple axes, wherein the electromechanical tool is configured to be mounted on, and move relative to, the electromechanical arm; and
   a control system configured to control movement and surgical functions of the end effector according to at least two control states in response to actuation of a user interface device, wherein:
   in a first control state, a movement of the user interface device in a first selected direction effects a corresponding movement of the end effector in the first selected direction; and
   in a second control state, a movement of the user interface device in the first selected direction does not effect a corresponding movement of the end effector in the first selected direction and the end effector performs a first surgical function in response to receipt of a first surgical function input by the user interface device; and
   the control system enters the second control state from the first control state in response to receipt of a first transition input by the user interface device.

2. The system of claim 1, wherein the control system enters the first control state from the second control state when a second transition input is received by the user interface device and a current position of the user interface device with respect to the first selected direction during the second control state is within a tolerance of a prior position of the user interface device with respect to the first selected direction when the second control state was entered from the first control state.

3. The system of claim 1, further comprising a vision system configured to display a current end effector position and a graphical representation of an estimated end effector position according to the current position of the user interface device.

4. The system of claim 1, wherein, in the first control state, movement of the end effector corresponds to movement of the user interface device in any direction.

5. The system of claim 2, wherein the control system is configured to control movements and surgical functions of the end effector according to a third control state in response to receipt of a third transition input by the user interface device, and wherein, in the third control state, movement of the user interface device in a second selected direction, different from the first selected direction, does not result in a corresponding movement of the end effector in the second selected direction and the end effector performs a second surgical function, different from the first surgical function, in response to receipt of a second surgical function input by the user interface device.

6. The system of claim 5, wherein the control system is configured to prohibit entry of the third control state from the second control state prior to performance of the second surgical function.

7. The system of claim 5, wherein the control system enters the second control state from the third control state when a fourth transition input is received by the user interface device and a current position of the user interface device during the third control state is within a tolerance of a prior position of the user interface device with respect to the second selected direction when the third control state was entered from the second control state.

8. The system of claim 7, wherein the second surgical function comprises at least two sequentially performed surgical functions and wherein the control system is configured to prohibit transition from the third control state to the second control state until each of the at least two surgical functions of the second surgical function is performed.

9. The system of claim 5, wherein the first surgical function comprises clamping the tissue and the second surgical function comprises deploying a plurality of staples to the tissue.

10. The system of claim 5, wherein the control system is configured to prohibit entry of the first control state from the third control state.

11. The system of claim 7, wherein the second transition input, the third transition input and the fourth transition input comprise modulation of the first transition input.

12. A method of controlling a surgical robot, the method comprising:
    receiving, by a computing device, an actuation signal corresponding to actuation of a user interface device;
    generating, by the computing device, a plurality of command signals in response to receipt of the actuation signal according to a first control state and a second control state, the plurality of command signals configured to control a surgical robot comprising an electromechanical arm, an electromechanical tool mounted to the electromechanical arm including an instrument shaft, and an end effector formed on the instrument shaft configured to perform a plurality of surgical functions on tissue of a patient, wherein:
    in the first control state, a movement of the user interface device in a first selected direction affects a corresponding movement of the end effector in the first selected direction;
    in the second control state, a movement of the user interface device in the first selected direction does not affects a corresponding movement of the end effector in the first selected movement direction and the end effector is configured to perform a first surgical function in response to receipt of a first surgical function input by the user interface device; and
    entering, by the computing device, the second control state from the first control state in response to receipt of a first transition input by the user interface device.

13. The method of claim 12, further comprising:
    storing, by the computing device, a first position representing a position of the user interface device with respect to the first selected direction at the time the second control state is entered; and
    entering, by the computing device, the first control state from the second control state when a second transition input is received by the user interface device and a current position of the user interface device with respect to the first selected direction is within a tolerance of the stored first position.

14. The method of claim 12, further comprising, by the computing device, generating a graphical representation of an estimated end effector position according the actuation signal that suitable for overlay upon an image of a current end effector position.

15. The method of claim 12, wherein, in the first control state, movement of the end effector corresponds to movement of the user interface device in any direction, including rotational movement.

16. The method of claim 12, wherein the computing device is configured to control movements and surgical functions of the end effector according to a third control state in response to receipt of a third transition input by the user interface device, and wherein, in the third control state, movement of the user interface device in a second selected direction, different from the first selected direction, does not result in a corresponding movement of the end effector in the second selected direction and the end effector performs a second surgical function, different from the first surgical function, in response to receipt of a second surgical function input by the user interface device.

17. The method of claim 16, wherein the plurality of command signals prohibit entry of the third control state from the second control state prior to performance of the second surgical function.

18. The method of claim 16, wherein the computing device is further configured to:

store a second position representing a position of the user interface device with respect to the second selected direction at the time the third control state is entered from the second control state; and enter the second control state from the third control state when a fourth transition input is received by the user interface device and a current position of the user interface device with respect to the second selected direction is within a tolerance of the stored second position.

19. The method of claim 18, wherein the second surgical function comprises at least two sequentially performed surgical functions and wherein the plurality of command signals prohibit entry of the second control state from the third control state until each of the at least two surgical functions of the second surgical function is performed.

20. The method of claim 16, wherein the first surgical function comprises clamping the tissue and the second surgical function comprises deploying a plurality of staples to the tissue.

21. The method of claim 16, wherein the plurality of command signals prohibit entry of the first control state from the third control state.

22. The method of claim 18, wherein the second transition input, the third transition input, and the fourth transition input comprise modulation of the first transition input.

* * * * *